(12) United States Patent
Paskar

(10) Patent No.: US 6,902,555 B2
(45) Date of Patent: Jun. 7, 2005

(54) SHAPEABLE CATHETER

(76) Inventor: Larry D. Paskar, 14337 Stablestone Ct., Chesterfield, MO (US) 63017

( * ) Notice: Subject to any disclaimer, the term of this patent is extended or adjusted under 35 U.S.C. 154(b) by 58 days.

(21) Appl. No.: 09/931,562

(22) Filed: Aug. 16, 2001

(65) Prior Publication Data

US 2002/0013547 A1 Jan. 31, 2002

Related U.S. Application Data

(63) Continuation-in-part of application No. 08/764,745, filed on Dec. 12, 1996, now abandoned, which is a continuation-in-part of application No. 07/834,007, filed on Feb. 11, 1992, now Pat. No. 5,304,131, which is a continuation-in-part of application No. 07/730,120, filed on Jul. 15, 1991, now Pat. No. 5,290,229.

(51) Int. Cl.⁷ ............................................. A61M 31/00
(52) U.S. Cl. ................................... 604/500; 604/95.04
(58) Field of Search ............................. 604/95.04, 523, 604/530, 532, 165.04, 500; 128/898; 606/1

(56) References Cited

U.S. PATENT DOCUMENTS

| | | | | |
|---|---|---|---|---|
| 4,430,083 A | * | 2/1984 | Ganz et al. | 604/523 |
| 4,474,174 A | * | 10/1984 | Petruzzi | 600/104 |
| 5,109,830 A | * | 5/1992 | Cho | 600/108 |
| 5,263,928 A | * | 11/1993 | Trauthen et al. | 604/509 |
| 5,267,982 A | * | 12/1993 | Sylvanowicz | 604/532 |

* cited by examiner

Primary Examiner—Mark Bockelman
(74) Attorney, Agent, or Firm—Husch & Eppenberger LLC

(57) ABSTRACT

A transformable catheter includes a sheath having a length which is a substantial fraction of the entire length of the transformable catheter and a bore therethrough. A preformed inner catheter having a complex curve formed into the distal end thereof is disposed in the sheath bore. By axially moving the inner catheter with respect to the sheath, various tip shapes may be achieved. At least one wire runs from the proximal end of the sheath to the vicinity of the distal end of the sheath to selectively deflect the distal tip of the sheath as desired by the user to assist in reformation and transformation of the tip of the catheter. By suitable manipulation of the wire and of the inner catheter with respect to the sheath, the shape of the exposed portion of the distal end of the inner catheter may be transformed to any of a variety of shapes.

44 Claims, 10 Drawing Sheets

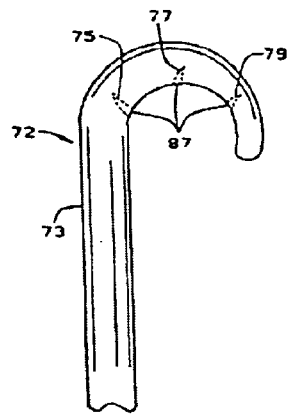
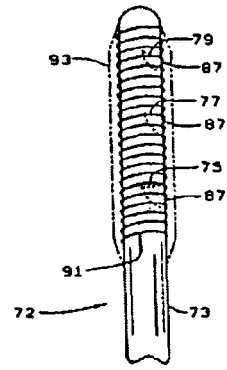
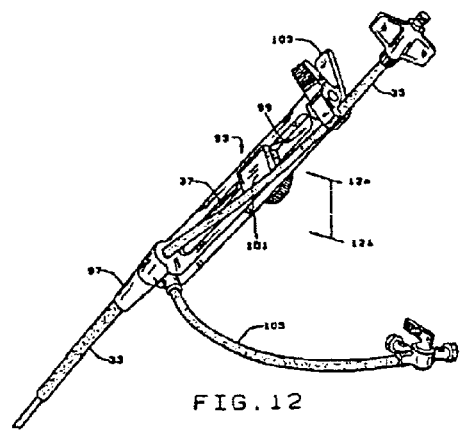
FIG.10   FIG.11   FIG.12
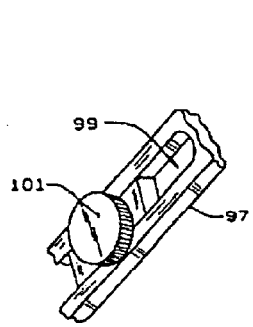
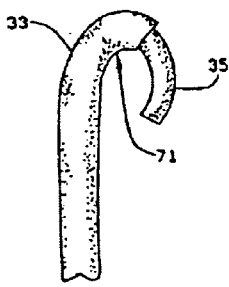
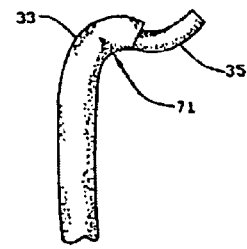
FIG.12A   FIG.13   FIG.14
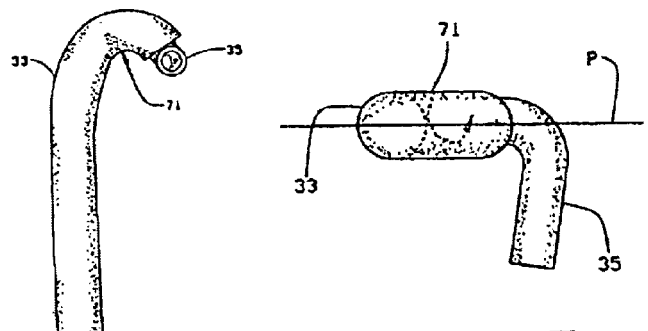
FIG.15   FIG.15A

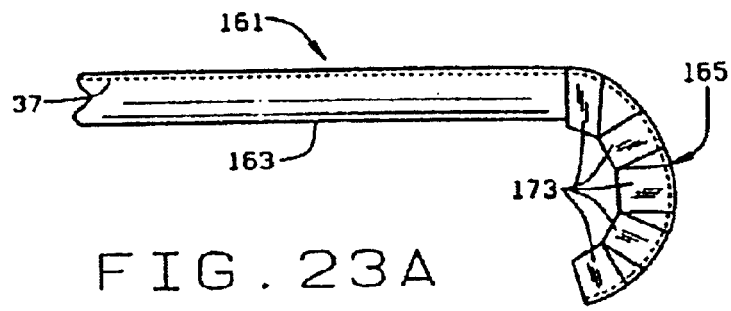
FIG. 23A
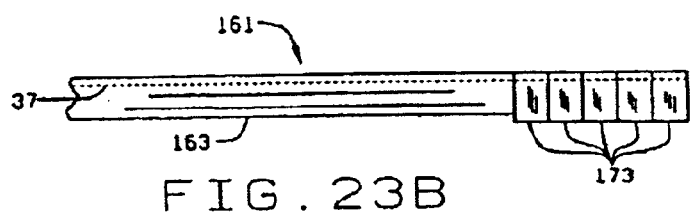
FIG. 23B
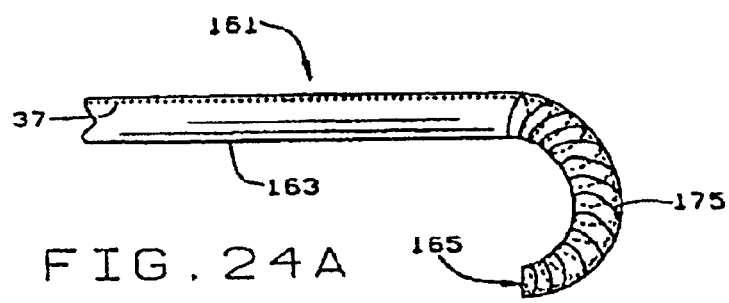
FIG. 24A
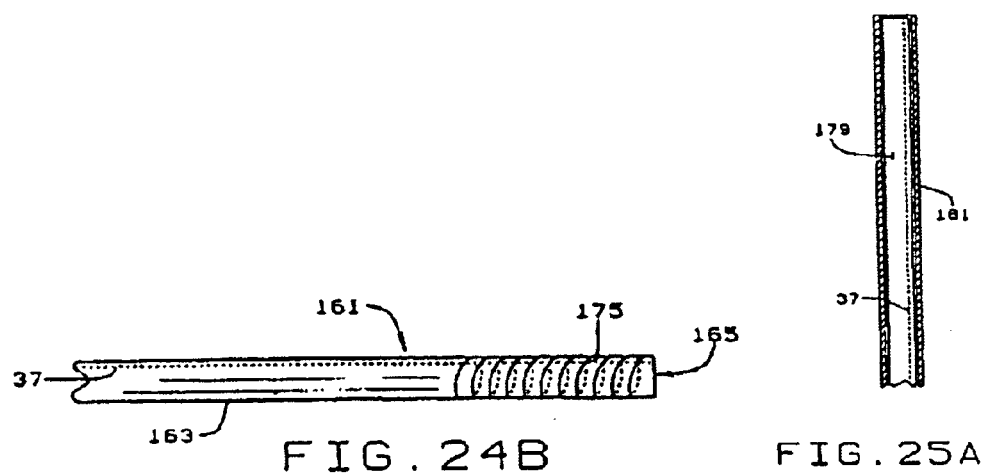
FIG. 24B
FIG. 25A

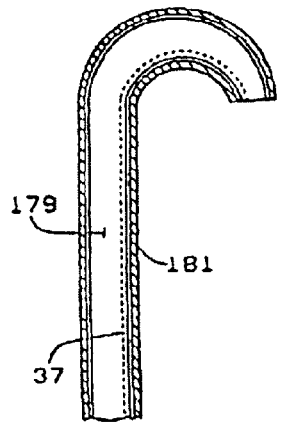
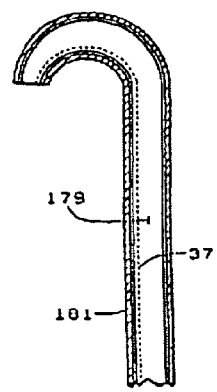
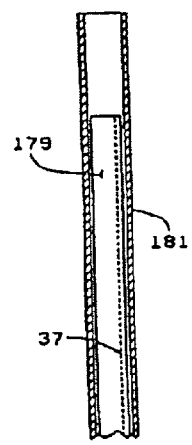
FIG. 25B   FIG. 25C   FIG. 26A
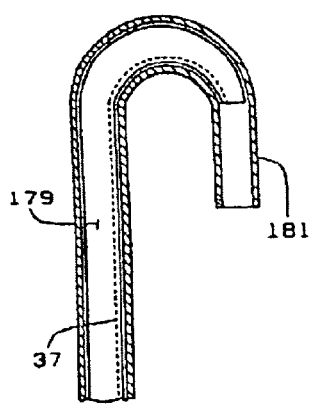
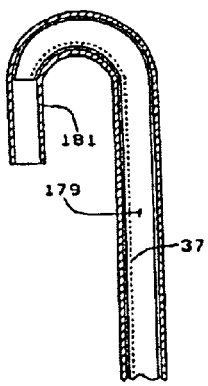
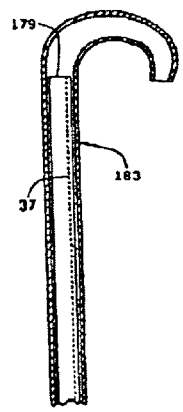
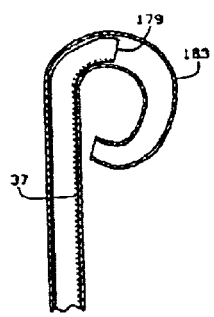
FIG. 26B   FIG. 26C   FIG. 27A   FIG. 27B
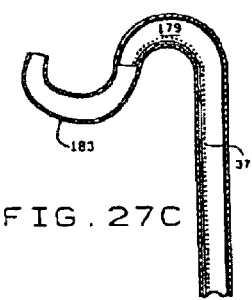
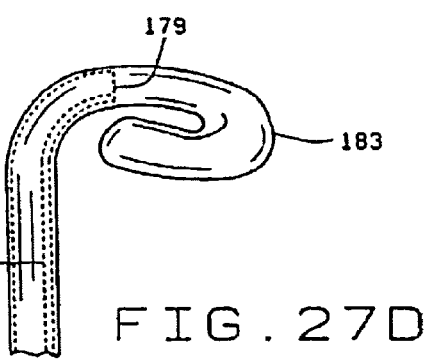
FIG. 27C   FIG. 27D

SHAPEABLE CATHETER

CROSS REFERENCE TO RELATED APPLICATION

The present application is a continuation-in-part of the U.S. application Ser. No. 08/764,745. filed Dec. 12, 1996; abandoned which is a continuation in part of the then U.S. application Ser. No. 07/834,007, filed Feb. 11, 1992, since issued as U.S. Pat. No. 5,304,131; which is a continuation in part of the then U.S. application Ser. No. 07/730,120, filed Jul. 15, 1991, since issued as U.S. Pat. No. 5.290,229.

STATEMENT REGARDING FEDERALLY-SPONSORED RESEARCH/DEVELOPMENT

Not applicable.

REFERENCE TO MICROFICHE APPENDIX

Not applicable.

BACKGROUND OF THE INVENTION

This invention relates generally to medical devices, and more particularly to a catheter which can be formed, inside the human body, into a vast number of different shapes.

Selective catheterization of cerebral and visceral branch arteries is often difficult and at times impossible in some patients—particularly older patients with very tortuous and ectatic vasculature. Successful catheterization sometimes requires multiple catheter exchanges for various shaped catheters. It is not uncommon to easily catheterize three of four vessels for a four vessel head study, only to find that the fourth vessel (generally the left or right carotid) requires an entirely different catheter shape and tip orientation. It would be desirable if one could easily and simply reshape the catheter and reorient the tip to direct it into the vessel orifice, instead of depending on several complex catheters that require reformation, fancy torque and advancing maneuvers, body english and, above all, luck.

Tip reorientation, the goal of most prior devices which have addressed the problem, is only half of what is needed to make a truly workable universal catheter. Numerous catheter curve configurations have been conceived not only to reorient the tip properly for selection of branch vessels, but also to provide anchorage of the catheter against the aortic wall. A wide looped long tipped sidewinder III configuration with an exaggerated retrocurve is one such example of a highly specialized complex catheter.

This anchorage or wedge effect against the aortic wall lessens the recoil caused by the "jet effect" during high pressure contrast injection which might otherwise cause the catheter to flip out of the selected branch vessel (particularly in short branch vessels or at levels of a dilated aorta).

These complex configurations, therefore, evolved not only to orient the tip properly, but also to wedge the catheter securely in the branch vessel. Other devices which simply modify the distal catheter curve may aid in tip orientation for vessel selection, but fail to provide the anchorage which is necessary to prevent catheter dislodgement.

In addition, prior designs could be improved in that the radii which the prior devices are able to make (to enter a vessel at a sharp angle, for example) have heretofore been severely limited.

Moreover, the size of prior designs has made them less desirable for many applications.

In certain applications (for example, complex interventional procedures such as angioplasties or intracerebral procedures), current catheters could be improved with respect to their ability to facilitate crossing of tight stenoses or with respect to their trackability out into peripheral branches.

In this respect, the current catheters could be improved in the areas of displacing forces from the application site at the point of catheter introduction (most often in the inguinal area) to points close to the actual catheter tip. This would increase the control that a user, such as an angiographer, has on the catheter, creating a more precise local longitudinal vector force for crossing tight stenoses, and also increase torque force for guiding the catheter tip toward the orifice of a selected vessel.

It would also be desirable to have a catheter construction which provided controllable variability in the distal catheter stiffness. Such a catheter could be stiffened for support close to a first order selected branch through which a more flexible catheter could be tracked peripherally. Conversely, such a catheter could be made less stiff over variable distances to allow better tracking of a more flexible distal end over a guidewire.

SUMMARY OF THE INVENTION

Among the various objects and features of the present invention may be noted the provision of a catheter which simplifies the catheterization procedure.

A second object is the provision of such a catheter which significantly reduces the number of catheterizations required for any particular medical procedure.

A third object is the provision of such a catheter which can be easily and simply reshaped into a variety of different shapes as desired by the user.

A fourth object is the provision of such a catheter which can mimic almost any catheter configuration, and can thereafter be reformed in the body to other desired shapes.

A fifth object is the provision of such a catheter which obviates the need for multiple catheter exchanges, thereby reducing the time involved in a medical procedure and also reducing the possibility of complications.

A sixth object is the provision of such a catheter which provides adequate anchorage of the catheter against the aortic wall to reduce the "jet effect."

A seventh object is the provision of such a catheter which is capable of achieving an improved curve radius at its distal end.

An eighth object is the provision of such a catheter which is significantly reduced in size compared to the prior devices.

A ninth object is the provision of such a catheter which will displace longitudinal vector force from the site of application in the groin of the patient to a point near the tip of the catheter, thereby facilitating the crossing of tight stenoses during angioplasty procedures.

A tenth object is the provision of such a catheter which will displace torque force from the site of application in the groin of the patient to a point near the tip to facilitate more precise torque of the catheter tip, improving the ability to enter selected vessels.

An eleventh object is the provision of such a catheter which will provide variable stiffness at the distal end that will facilitate catheter advancement peripherally when it serves as a stiffened support near a first order take off vessel and will likewise facilitate tracking over a guidewire when made more flexible over a variable distance, distally.

A twelfth object is the provision of a method of shaping a combination catheter in a passage in the human body.

A thirteenth object is the provision of a method of shaping a combination catheter in a passage in the human body during fluoroscopic imaging.

Other objects will be in part apparent and in part pointed out hereinafter.

Briefly, a combination catheter of the present invention includes a catheter tube having a wall and an internal lumen extending substantially through the length of the catheter tube. The catheter tube has an outside diameter sufficiently small so that the catheter tube may be inserted into the human body and has a proximal end and a distal end. The catheter tube also has a remotely controlled deflectable distal tip and a substantially uniform transverse cross section throughout a substantial part of its length. The catheter tube wall adjacent the distal end of the catheter tube has a predetermined reference position therein on one side of the longitudinal axis of the catheter tube. An inner surgical element is disposed in the lumen of the catheter tube, the inner surgical element being rotationally and axially movable in the lumen of the catheter tube and being sufficiently pliable to bend upon bending of the catheter tube. Manually operable structure is provided for fixing the inner surgical element in desired rotational positions with respect to the catheter tube.

In a second aspect of the present invention, a transformable catheter includes a sheath having a diameter sufficiently small so that the sheath may be inserted into blood vessels of the human body. The sheath has a length which is a substantial fraction of the entire length of the transformable catheter, a bore therethrough running substantially from the proximal end of the sheath to the distal end of the sheath, and a remotely controlled deflectable distal tip. A preformed inner catheter sized to fit in the sheath bore is axially and rotationally movable with respect to the sheath in the bore, whereby by suitable manipulation of the inner catheter with respect to the sheath and of the distal end of the sheath the shape of the exposed portion of the distal end of the inner catheter may be reformed and transformed to any of a variety of shapes as desired by the user. Manually operable structure is provided for fixing the catheter in any desired rotational and/or longitudinal position with respect to the sheath.

Another aspect of this invention provides a method of shaping a combination catheter (wherein the combination catheter comprises an inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said lumen and being axially movable with respect to the catheter tube, at least one of said catheter tube and said inner medical element being remotely controllable to form a curve in the distal end thereof) comprising moving the combination of the catheter tube and the inner medical element in a passage in the human body to a desired position (the moving occurring with the distal end of the inner element disposed distally of the distal tip of the catheter tube); imaging the catheter tube and the inner medical element while said tube and medical element are disposed in the human body; shaping the distal end of the combination catheter during the imaging of the catheter tube and the inner medical element by manipulating the distal end of the combination catheter such that the distal end of the combination catheter takes a desired shape; and then verifying the desired shape by imaging the catheter tube and the inner medical element. The imaging in this process can be done by fluoroscopy.

This method allows for an inner medical element which can be remotely controllable to assume curved configurations.

Although the invention is described in connection with blood vessels, it is not so limited. It may be used not only in arterial and venous structures, but also in the biliary tree, urinary tract, body cavities (such as the thorax and abdomen), hollow viscus organs (such as the stomach, intestines, and urinary bladder), cysts and abscesses—in short, in any place where selective direction and reformation of a catheter, tube or guidewire is required.

BRIEF DESCRIPTION OF THE DRAWINGS

FIGS. 10 and 11 illustrate the method of construction of an alternative to that of FIGS. 4A–4D;

FIGS. 12 and 12A are perspective views illustrating an improved handle of the present invention;

FIG. 13 is a side elevation of a transformable catheter of the present invention illustrating one achievable shape;

FIG. 14 is a side elevation of the transformable catheter of FIG. 13 illustrating a second achievable shape;

FIG. 15 is a side elevation of the transformable catheter of FIG. 13 illustrating a third achievable shape;

FIG. 15A is a top plan of the catheter of FIG. 15;

FIGS. 23A and 23B are views similar to FIGS. 21A and 21C showing a segmental band construction for the sheath;

FIGS. 24A and 24B are views similar to FIGS. 21A and 21C showing a coil spring construction for the distal end of the sheath;

FIGS. 25A–25C are side elevations, with parts broken away, of a manipulator of the present invention used in combination with an outer catheter;

FIGS. 26A–26C are views similar to FIGS. 25A–25C showing the outer catheter in a distally extended position with respect to the manipulator;

FIGS. 27A–27C are side elevations, with parts broken away, of a manipulator of the present invention used in combination with an outer catheter having a curved distal end; and FIG. 27D is a side elevation of the manipulator/catheter combination of FIGS. 27A–27C with the manipulator rotated ninety degrees with respect to the curvature of the outer catheter.

Similar reference characters indicate similar parts throughout the several views of the drawings.

DESCRIPTION OF THE PREFERRED EMBODIMENT

Figure 1A:
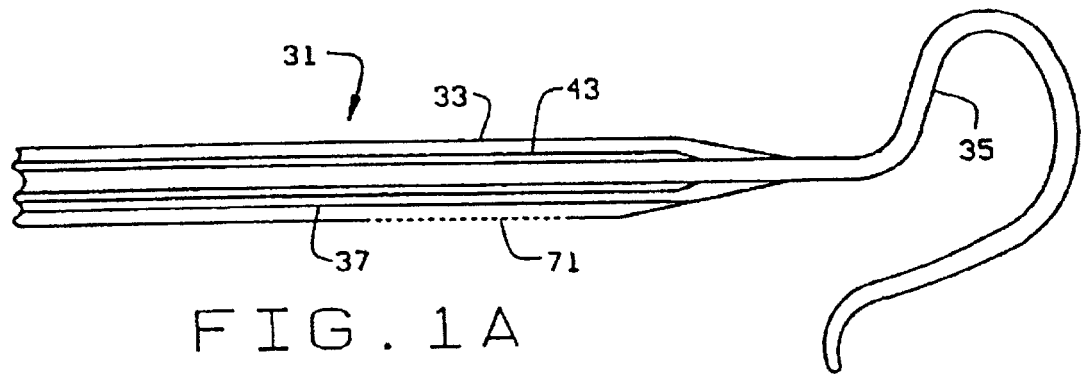
FIGS. 1A–1B, and 1D are side elevations illustrating the construction of the transformable catheter of the present invention.
Figure 1B:
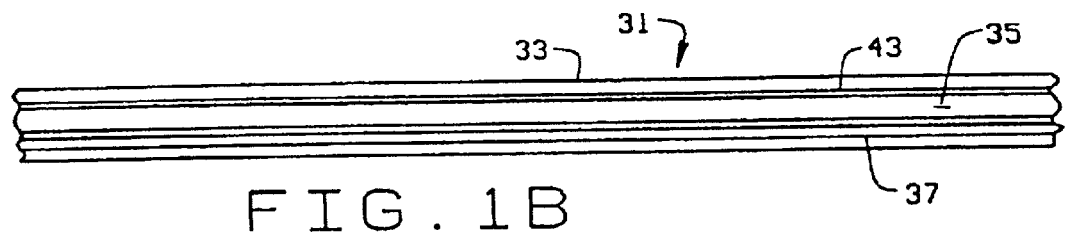
Figure 1C:
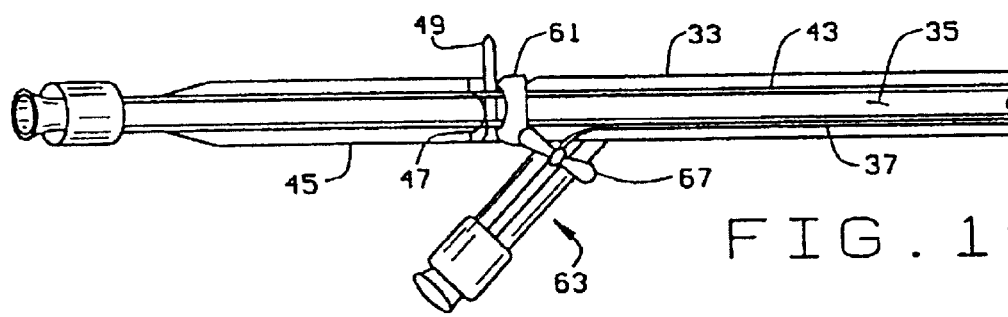
FIG. 1C is a top plan of the proximal portion of the transformable catheter of the present invention.

A catheter 31 (see FIGS. 1A–1C) of the present invention in its simplest form includes an enabling sheath 33, and an inner catheter 35 having a distal tip with a complex-curve shape. Catheter 31 is especially suited for selective arterial catheterization. In that application, the catheter is custom shaped or formed while in the patient to make it easy to direct the tip in any orientation required to enter a branching orifice or serpiginous vessel. Catheter 31 is not simply a steerable catheter, but also one which may be custom curved and recurved by the user to select each branch vessel. The catheter may also be used in the biliary tree and urinary tract to negotiate branches, corners, and serpiginous pathways.

As will become apparent in view of the following disclosure, manipulation of catheter 31 results in mimicking virtually any simple or complex curved configuration of selective arterial catheter shape imaginable while the catheter is disposed in the patient. Likewise, modification of curve and tip orientations allow selection and direction of wire guides for other invasive procedures such as percutaneous cholangiography and percutaneous nephrostomy; that is, any procedure requiring direction or redirection of a catheter.

Inner catheter 35 is a complex memory curve catheter which runs in a coaxial manner through enabling sheath 33. With the complex tip completely extended beyond the sheath, the most complex tip configuration reforms. By pulling the inner catheter back through the enabling sheath to varying degrees (sheathing and unsheathing the inner catheter tip), various segments of the curve are straightened or "ironed out"—thereby changing the overall catheter tip configuration and tip orientation. The inner catheter is the active primary component but is a passive passenger with respect to the enabling sheath which acts upon the catheter to modify its shape. In addition, the fact that the transformation takes place in a vessel in the human body further modifies the shapes which can be achieved due to interaction of the transformable catheter with the walls of the vessel.

Sheath 33 has the capability of being formed by a pullwire 37 into a hook configuration, as described below. (Although described as a wire, item 37 could equivalently be made of high tensile strength suture or thread material.) This capability allows reformation of the complex memory curvature by directing the catheter tip downward while transformable catheter 31 is disposed in the abdominal aorta. Secondarily the sheath curve can, to varying degrees, act on the catheter to further modify the catheter shape.

In detail, transformable catheter 31 (see FIGS. 1A–1C) includes outer enabling sheath 33 which extends almost the entire length of the catheter. It is preferred that sheath 31 be long enough so that only the complex curve distal end portion of the inner catheter extend beyond it. Inner catheter 35 is disposed in the central bore of sheath 33 and has the most exaggerated sidewinder preformed tip configuration distally. (Of course, any other similar complex-shaped memory curve inner catheter could also be used in the present invention as inner catheter 35.) The distal end of enabling sheath 33 can be formed into a curve with up to one hundred and eighty degrees of curvature when retracted by pull wire 37 by the suitable application of tension to the pull wire. This allows the hook configuration of the sheath 33 to reform the catheter 35 when the catheter is advanced through the sheath. The variable curved tip also allows variation in the degree of curvature, modifying the natural memory curve and thereby the overall shape of the catheter. Although pull wire 37 is the preferred structure for remotely controlling the deflection of the distal tip of sheath 33, any suitable structure such as guide wires, probes, or the like may be used. Moreover, if sheath 33 is formed with a curved distal end, a fairly rigid straight probe may be inserted into the sheath to straighten out the distal end of the sheath the desired amount. Other structures for performing this function will also be apparent to those of ordinary skill in the art.

Figures 2A, 2B, 2C, 2D:
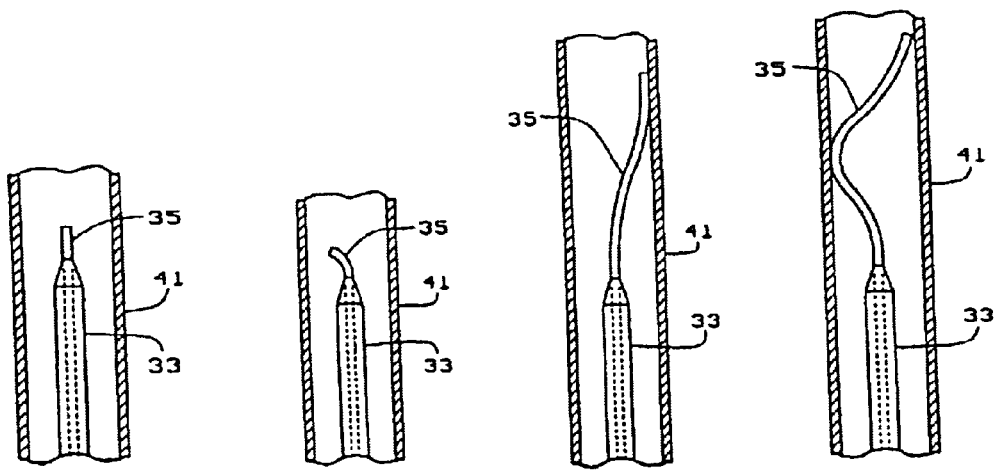
FIGS. 2A–2D are simplified elevations illustrating some of the myriad shapes which are attainable with the transformable catheter of the present invention.

Enabling sheath 33 modifies the extreme natural curvature of catheter 35 by acting as a housing that irons out various segments of the curvature when the catheter is retracted back into the sheath. Such an ironing" effect is illustrated in FIG. 2A. In FIGS. 2 and 3, the various portions of transformable catheter 31 are shown in simplified form for clarity. For example, in FIG. 2A, the catheter 35 is shown extending distally from sheath 33 a small amount, while catheter and sheath are disposed in a vessel (such as an artery) 41.

In FIG. 2B, the same catheter 35 is shown extended distally out of sheath 33 a small additional amount such that the catheter regains some of its curvature. Similarly, in FIGS. 2C and 2D, catheter 35 is extended distally even further. Note that in FIG. 2D, the distal curved portion of catheter 35 is fully extended from sheath 33, but the original configuration of catheter 35 is not obtained because of the interaction of the catheter with vessel wall 41.

Figures 3A, 3B, 3C:
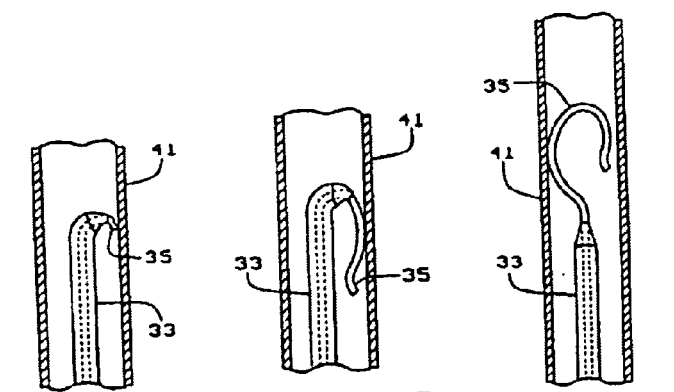
FIGS. 3A–3C are simplified elevations illustrating the reformation of a complex catheter shape inside the human body.

If the physician desires to instead shape or form catheter 35 back into its original, preformed shape of FIG. 1, the steps illustrated in FIGS. 3A–3C are followed. In this case, the sheath is first formed (by use of retraction wire 37) into the shape shown in FIG. 3A and FIG. 3B. As a result of this shape of the sheath, as catheter 35 is moved distally with respect to the sheath it assumes the form in the vessel as illustrated in FIGS. 3A and 3B. The sheath is restraightened by suitable manipulation (i.e., release) of retraction wire 37 as shown in FIG. 3C as desired. This procedure allows the original form of catheter 35 to be obtained in the vessel.

Note, from comparing FIG. 2D with FIG. 3C, the great differences in catheter shape achievable by simple manipulation of sheath 33 and of the catheter with respect to the sheath. In fact FIGS. 2A–2D and 3A–3C all illustrate some of the multitude of different catheter shapes which may be formed in the body, during a medical procedure, using the present invention. It should be realized that these shapes are merely illustrative and that with suitable manipulation of the sheath and relative movement between the sheath and the catheter, a great number of additional catheter configurations may be achieved.

Note as well, that the particular configuration shown in FIG. 3B provides a tighter radius for the tip of catheter 31 than is achievable with prior devices due to the interaction of complex-formed tip of the inner catheter and the deflection of the sheath. This greater flexibility in the shapes achievable permits vessels to be entered with the present catheter which were not readily accessible with the prior devices.

Referring back to FIGS. 1A–1C, the inner catheter 35 travels through the enabling sheath in a coaxial manner, but is stiffened from its proximal end to a point just proximal to the distal exaggerated curvatures by an outer stiffening segment 43. This outer stiffening segment is fused to the inner catheter proximally and distally and provides sufficient strength to the inner catheter to permit it to be moved axially with respect to the sheath without collapsing or binding.

Transformable catheter 31 is introduced in the usual manner through the femoral artery and advanced into the abdominal aorta. The catheter is reformed and selectively shaped in the abdominal aorta. When initially introduced the inner catheter is in its straightened parked position within the enabling sheath with only a small distal tip segment protruding (see FIG. 2A). The pull wire 37 is retracted, forming a hooked curve (see FIG. 3A) which allows direction of the catheter tip downward and thereby easy reformation of the memory curve. Once reformed, the various shapes of the catheter can be selected by advancing or retracting the catheter into the enabling sheath, thereby allowing or disallowing the natural memory curves to form at various segments. Pull wire modification of the enabling sheath allows additional curved configurations.

Figure 1D:
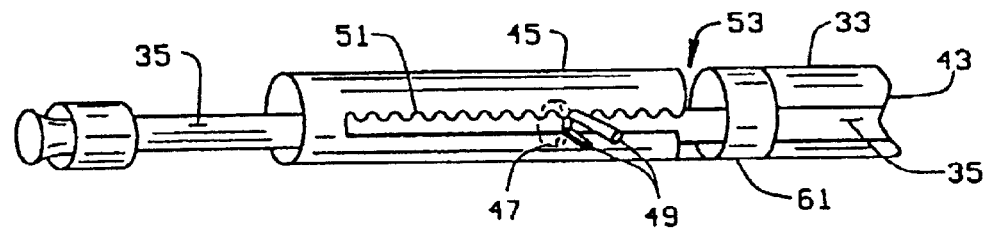
Figure 1E:
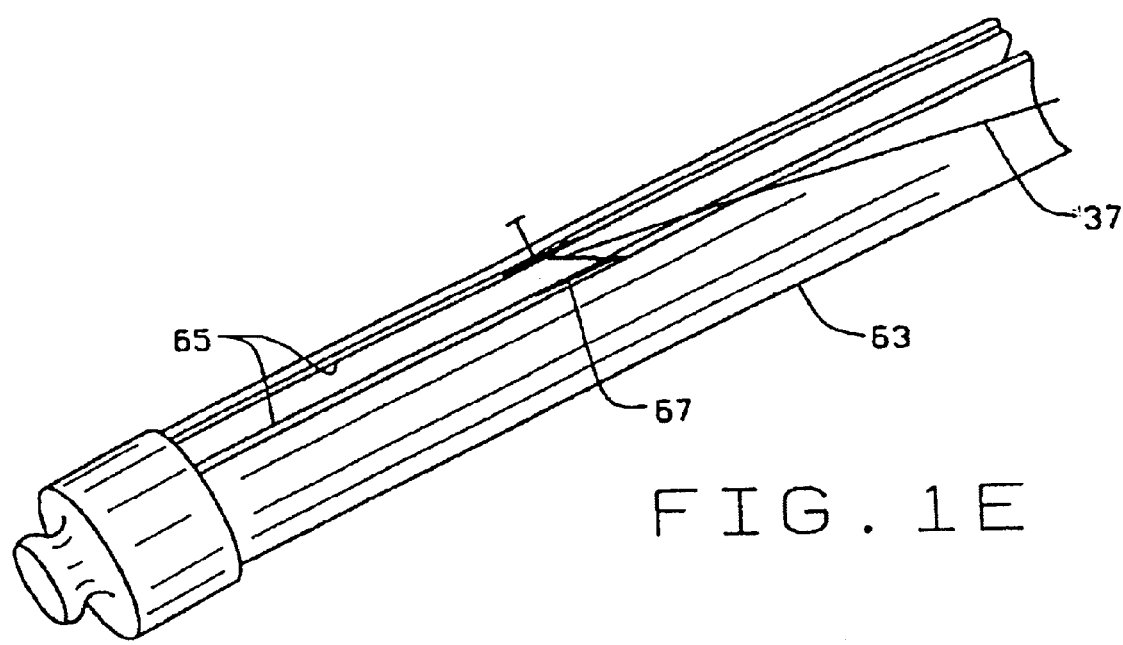
FIG. 1E is a view, similar to FIG. 1D but on an enlarged scale, illustrating the construction of a side port of the transformable catheter of the present invention.

Proximally, the stiffened inner catheter is pulled back through a plastic sleeve 45, slotted on either side. (See FIGS. 1C and 1D.) A fixation collar 47 attaches to the proximal portion of the catheter. A molded spring "V" prong 49, rounded on one side and flat on the other, arises from the side of the collar and extends through the sleeve. The prong is fixedly secured to catheter 35 and can be pulled through a right slot 51 of the sleeve (see FIG. 1D), thereby pulling the catheter as a whole through the enabling sheath and ironing out various degrees of memory curve in the distal tip of the catheter. The spring "V" prong 49 when squeezed together passes freely through the slot whose border is straight inferiorly but serrated superiorly as shown in FIG. 1D. When released the prong springs open and the rounded segment locks in a chosen serrated position. Distally, a crossing slot 53 allows the prong to be pulled across to the left slot (similar in size and shape to the right slot 51 shown), thereby twisting and torquing the entire catheter one hundred and eighty degrees so that when the prong 49 is pulled back in the left slot position the curved configuration is ironed out, resulting in additional variations in catheter shape. The locking pattern of the left slot is opposite to that of the fight-flat upper border, serrated lower border, still allowing collar locking in various retracting positions.

The inner catheter proximally must exit through a valve (such as hemostasis valve 61 shown in FIG. 1C) as found in current arterial sheaths. A "Y" branch side port 63 allows constant pressure flushing of the sheath to prevent possible clot formation and allows water activation of the hydrophilic retraction wire.

On top of the side port 63, slide tracks 65 (see FIG. 1E) are molded. The tracks contain a plastic "S" spring slide 67 with locking teeth. The slide spring is attached to the pull wire 37 proximally. As the slide spring is disengaged by pushing downward and pulling back, the wire is retracted. When released the "S" slide locks into the selected position in the track. When straightening of the enabling sheath is desired, the slide 67 is disengaged and pushed to the forward position, thereby releasing traction on the wire and allowing the enabling sheath to reform spontaneously or with help by sliding the reinforced catheter towards the tip or by placing a straightening wire guide through the inner catheter lumen.

The ventral primary curvature segment of the enabling sheath is biased (as indicated at the reference numeral 71, FIG. 1A) to curve in a desired direction by making the sidewall along the inner portion of the desired curve more flexible due to the type or thickness of the material in this segment. Similarly, a flexibility bias can be established by designing exposed or covered gaps along one side of a segment of the sheath over which the bend is desired. When the wire is pulled, the more flexible or gapped side of the segment will give first, thereby, allowing curvature in a precisely selected segment and direction. Alternatively, the bias can be created merely by the placement and attachment of the pull-wire.

Although heretofore the invention has been described with respect to a transformable catheter with a controllable sheath and a complex curved inner catheter, the present invention is not so limited. The inventive aspects of the controllable sheath are applicable in general to medical tubing, including catheters. It should be understood, therefore, that a reference herein to "sheath" should be understood in the broader sense of medical tubing, which includes catheters.

It should be noted that the present construction provides improved torqueability (for guiding the catheter tip reliably to the desired orifice) and improved transfer of longitudinal forces (for crossing tight stenoses). When used as a combination catheter, the stiffer outer guide catheter and the more flexible inner surgical element displaces these forces from the remote point of application at the entry site (most often, the groin) to the distal end of the combination catheter at a point very close to the target area of interest. When used in this manner, advancing the stiffer outer element (the sheath) increase the stiffness of the distal end of the catheter as a whole. Retracting the outer element leaves more of the flexible inner surgical element exposed as the distal end, which provides improved trackability over a guidewire (not shown).

Figure 4A:
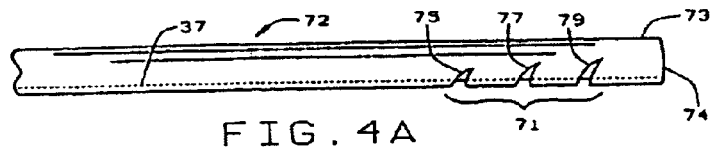
FIGS. 4A–4D are partial elevations illustrating operation of one embodiment of the present invention.

Turning to FIG. 4A, a sheath or catheter 72 of the present invention includes a medical tube 73 having an exterior wall and an internal lumen extending substantially through the length of the tube. The tube has an outside diameter sufficiently small so that it may be inserted into the human body. The distal end 74 of tube 73 is shown in FIG. 4A.

Wire 37 runs from the proximal end of the tube to the vicinity of the distal end of the tube, and, in the same manner as described above in connection with FIG. 1, is connected to the tube adjacent the distal end so as to allow the distal tip of the tube to be deflected upon movement of the wire. The tube has a substantially uniform transverse cross section throughout a substantial part of its length, except for the distal tip section. The tube wall adjacent the distal end has gaps 75, 77, and 79 therein on one side of the longitudinal axis of the catheter tube so as to form a predetermined region of weakness or zero reference position 71. As a result, upon tension being applied to the wire the distal end of the catheter tube bends in the direction of the predetermined region of weakness.

Figure 4B:
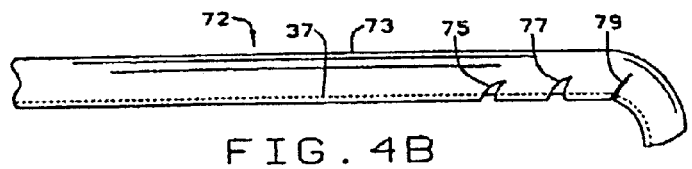
Figure 4C:
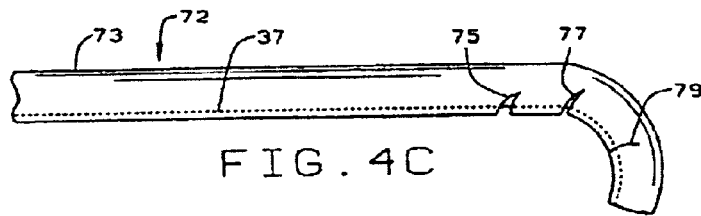
Figure 4D:
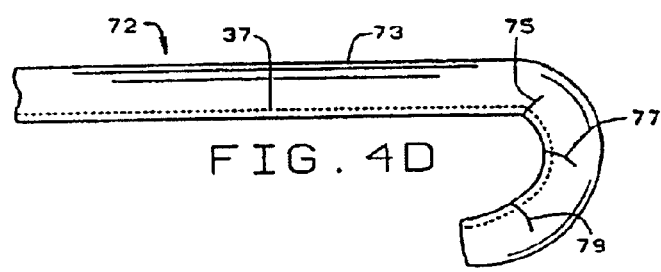

Although gaps 75, 77, and 79 can all be the same size, it is preferred that they differ in size as shown in FIG. 4A. The three gaps of FIG. 4A differ in depth, as can readily be seen. It has been found that with this construction the catheter or sheath preferentially bends first at the gap with the greatest depth (gap 79), and next at the gap with the second greatest depth (gap 77), and finally at the gap with the least depth (gap 75), as shown in FIGS. 4B–4D, as increasing tension is applied to wire 37.

Figure 5:
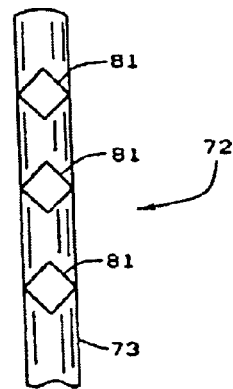
FIG. 5 is a partial elevation illustrating a gap shape different from that shown in FIGS. 4A–4D.
Figure 6:
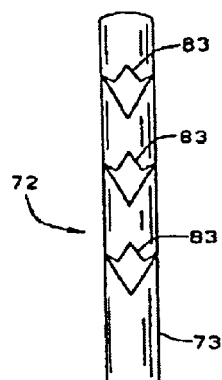
FIG. 6 is a view similar to FIG. 5 illustrating another gap shape.

Although gaps 75, 77 and 79 of FIG. 4 are generally crescent moon shaped, the present invention is not limited to any particular gap shape. For example, gaps 81 having a generally diamond shape (FIG. 5), or gaps 83 having a compound, arrowhead shape (FIG. 6), or any of a number of other gap shapes may also be used. Gaps shaped so that portions of the catheter tube wall on opposite sides of each gap may overlap when the catheter is formed by the wire to have its greatest curvature may be used, as may gaps shaped so that there is no overlap (although overlapping can provide a tighter curve on the distal end of the sheath/catheter). Similarly, gaps shaped so that the distal wall portion overlaps the proximal wall portion of the gap when the catheter is formed by the wire to have its greatest curvature may be used, as may gaps shaped so that the proximal wall portion overlaps the distal wall portion of the gap.

Figure 7:
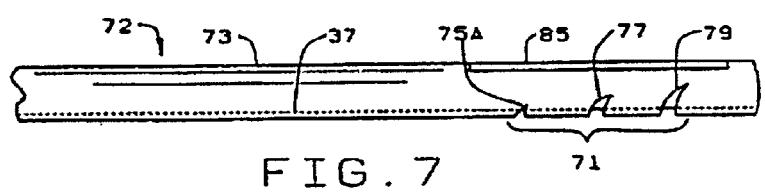
FIG. 7 is a view similar to FIG. 4A illustrating an alternative construction.

Nor is there any rigid requirement concerning depth of gap. Although the gaps of FIG. 4 extend through the walls of the sheath/catheter to the lumen, that is not a requirement. In FIG. 7, for example, a gap 75A is provided which terminates short of the sheath/catheter lumen. It still helps provide the desired predetermined region of weakness 71. Also shown in FIG. 7 is a reinforcing section 85 which may, for example, be co-extruded with the sheath/catheter. This reinforcing section may be used in combination with the gaps, or by itself, to cause the distal end of the sheath/catheter to bend in the direction of region 71 when tension is applied to wire 37.

No matter what the shape of the gap, it is preferred that the inner surface of the gap adjacent the lumen of the catheter be smooth.

Figure 8:
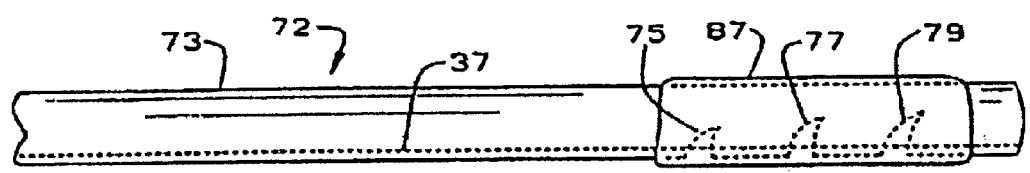
FIG. 8 is a view similar to FIG. 4A showing a covering over the gaps.

For some applications, it may be preferred that the gaps be covered. FIG. 8 shows a layer of material 87 covering the gaps. It should be realized that the physical appearance of layer 87 in FIG. 8 is illustrative only. The appearance will differ depending upon how layer 87 is made. It can be formed by dipping, fusing, or heat shrinking, for example.

Similarly, the gaps themselves may be formed in a number of different ways. They can be laser cut, water jet cut, punched, or formed by any other suitable procedure.

Figure 9:
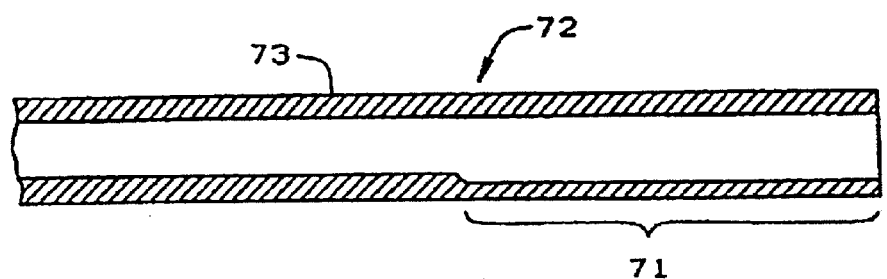
FIG. 9 is a sectional view illustrating an alternative way to cause the catheter to bend in a desired direction.

In addition, various ways can be used to form the predetermined region of weakness 71, either alone or in combination with the gaps. For example, FIG. 9 shows a region of weakness 71 formed by reducing the thickness of the sheath/catheter wall at the predetermined region of weakness. Or, the predetermined region of weakness may be formed by having a portion of the wall which is chemically different from the tube wall elsewhere, or otherwise differs in some way from the rest of the sheath/catheter wall. This is accomplished, for example, by leaching material out of the appropriate portion of the sheath/catheter wall to form the region of weakness, or by using a different material in that region which is weaker than the material which makes up the rest of the sheath/catheter wall.

It should be appreciated that when gaps 75, 77 and 79 are cut into a straight sheath/catheter, and the layer 87 put over those gaps, there is the possibility that layer 87 material will bulge into the inner lumen of the sheath/catheter when the distal end is curved by application of tension to wire 37.

This bulging can be prevented if the distal end of the catheter tube is preformed into a curved shape with the gaps on the inner side of the preformed curve, as shown in FIG. 10. The gaps are then in their "rest" position" when the distal end of the sheath/catheter is fully curved. A stretchable covering material 87 is then deposited over the gaps in this curved, "rest" position, so that the stretchable covering layer is substantially relaxed when the tube is disposed in a predetermined bent position.

With this construction, the stretchable covering layer 87 is substantially in tension when the distal end of the sheath/catheter is straight, and the covering layer tends to pull the distal end back to the preformed, curved shape. To overcome this tendency, a spring (or other suitable device) 91 is provided for biasing the stretchable covering layer into a stretched position, as shown in FIG. 11 Note that when the sheath/catheter is curved, the coils of the spring along the inner curve are closed while the coils along the outer curve are opened. A jacket of material 93 is provided to cover the biasing spring.

Turning to FIGS. 12 and 12A, it is desirable to make the transformable catheter of the present invention as easy to use as possible. To facilitate this, a handle assembly 95 is provided which is an alternative to the structure shown in FIGS. 1C–1E. Handle assembly 95 includes a handle 97 fixedly secured to sheath 33. Handle 97 has a slot 99 formed therein in which rides a thumbwheel operated clamp 101 (shown in more detail in FIG. 12A). The body of the thumbwheel operated clamp is connected to wire 37, so that the user may manually adjust the tension on wire 37 by moving clamp 101 to the desired position in slot 99 and fix the clamp in that position to maintain the desired tension on the wire. Since the position of clamp 101 in slot 99 is infinitely variable, the tension on wire 37 is also continuously variable over the desired range.

The construction of FIG. 12 also provides for infinite variation in the rotational and longitudinal positioning of catheter 35 with respect to handle 97. The handle has secured thereto a spring clamp 103. Catheter 35 may be held by the jaws of spring clamp 103 (or other suitable device) in any desired rotational or longitudinal position, as controlled by the user. The jaws of the clamp are merely opened to allow the user to move the catheter longitudinally and/or rotationally, and then closed on the catheter to hold it in the new desired position.

Also shown in FIG. 12 is an auxiliary line 105 which constitutes means (in combination with a pressure infusion, for example) for forcing fluid between the sheath 33 and the catheter 35. Such flushing helps to prevent the formation of clots, for example.

Figure 13A:
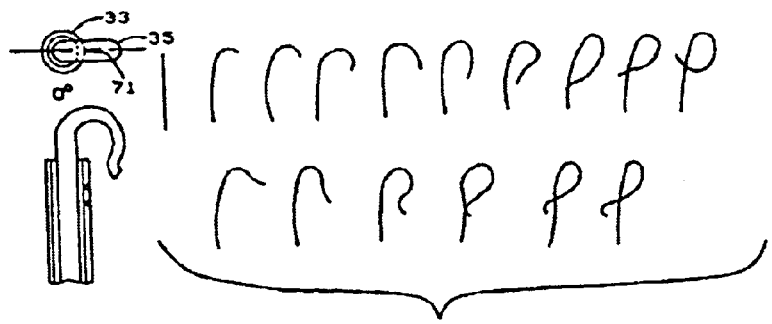
FIG. 13A is a diagrammatic representation of a family of shapes similar to that of FIG. 13.

The transformable catheter of the present invention is capable of achieving entire separate families of shapes. As shown in FIG. 13, when the inner catheter or element 35 is held in a first rotational position with respect to the longitudinal axis of the predetermined reference position 71 such that the curve of the inner catheter is aligned with the predetermined reference position (which may be considered a 0° position), the inner catheter 35 is formed into a downward going shape. This shape, it should be understood, is just one of a family of shapes achievable when the inner catheter is in the first rotational position with respect to the predetermined reference position. The other shapes in that family are achieved by bending the sheath more or less and exposing more or less of the inner catheter or element. See FIG. 13A.

Figure 14A:
FIG. 14A is a diagrammatic representation of a family of shapes similar to that of FIG. 14.

A second family of curves is illustrated by the same transformable catheter shown in FIG. 14. The catheter of FIG. 14 differs from that of FIG. 13 only in that the inner catheter or element is rotated approximately 180 degrees with respect to the predetermined rotational reference position. This causes the shape of the exposed inner catheter or element to be opposed to the direction of the bend in the sheath, resulting in the generally upward going shape shown in FIG. 14. Other shapes of this second family are achieved by bending the sheath more or less and exposing more or less of the inner catheter or element. See FIG. 14A.

Figure 15B:
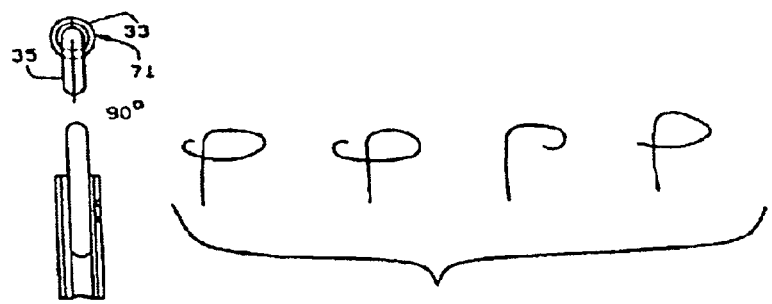
FIG. 15B is a diagrammatic representation of a family of shapes similar to that of FIG. 15.

In both FIGS. 13 and 14, the inner catheter or element is basically disposed in the plane of the predetermined region of weakness of the sheath. That is not the case, however, when the inner catheter or element is fixed at some intermediate rotational position, such as ninety degrees, with respect to the longitudinal axis of the predetermined region of weakness of the sheath, as shown in FIGS. 15 and 15A. The curved nature of the inner surgical element in this circumstance causes the exposed end of the inner surgical element to be disposed substantially out of the plane P containing the predetermined rotational reference position. Again, a whole family of these "out of plane" curves can be achieved as desired by the user by curving the sheath more or less and exposing more or less of the inner catheter or element. See FIG. 15B.

To summarize, because the outer element or sheath 33 has an orientation (it bends toward the predetermined reference position 71), and because the inner surgical element or catheter 35 has a complex shape, rotating the inner surgical element with respect to the sheath results in entire new families of catheter shapes—shapes heretofore not achievable with a single device. This provides extreme versatility to the present invention since it permit a vast number of different shapes to be made with one inner surgical element, one curvable sheath, and suitable manipulation of both. It should be appreciated that a large number of achievable shapes is desirable not only for entering different vessels by "banking" off the vessel walls into the desired vessel, but also for anchoring the catheter in place against a vessel wall during use.

Rotational movement of the elements is especially significant since it provides more versatility to the present device—allowing completely different curves to be achieved. Because rotation of the inner surgical element changes the geometrical relationship of the inner catheter with respect to the bias or predetermined reference position of the sheath or outer element, that rotation in combination with bending of the sheath at the predetermined reference position results in whole new families of achievable shapes for every rotational position.

The present device is unique in that it involves three functions or degrees of freedom which may be controlled independently but interact interdependently, resulting in almost limitless combinations and permutations—a vast number of catheter shapes. These functional variables when applied to different degrees result in almost any desired curve configuration. Other devices are not believed to even approach the capabilities of the present invention. The combination catheter disclosed is capable of reproducibly forming any number of shapes during a single medical procedure which are not achievable with the prior art devices. It can achieve the upgoing shapes shown in FIG. 14A, the down-going shapes shown in FIG. 13A, the out of plane shapes shown in FIG. 15B, and the tighter radius shapes shown in the lower right-hand portion of FIG. 13A.

Figure 16:
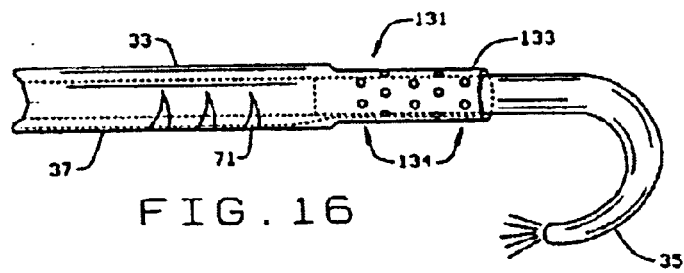
FIG. 16 is a side elevation of another embodiment of the combination catheter of the present invention.
Figure 16A:
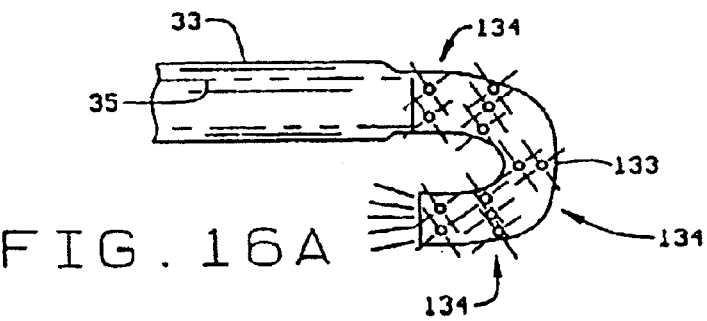

Turning to FIG. 16, there is shown a modified version 131 of the combination catheter of the present invention. Sheath 33 in this embodiment includes a distal end 133 having a plurality of side holes 134. The inner catheter 35 in this embodiment is of any desired shape at its distal end, with a end hole or opening for the passage of liquid, such as contrast media, therethrough. A desired liquid is injected through the inner catheter and, when the combination catheter is in the configuration shown in FIG. 16, the liquid passes out the distal end of the inner catheter. This configuration is used for selective arterial injection, However, when the inner catheter is withdrawn into sheath 33 to the position shown in phantom in FIG. 16, the liquid passes out through the multiple side holes 134 as well as out the distal end of the sheath. If the sheath is pulled into a hooked type coil and the inner catheter withdrawn to a position proximal the multiple side holes 134 (see FIG. 16A), the combination catheter of FIG. 16 mimics the side and end hole pigtail catheter suitable for aortic and ventricular injections. The side holes and the hook configuration of the sheath prevent dangerous whipping of the catheter during pressure delivery of a large bolus of contrast media. The multiple holes allow a greater volume of contrast media to be delivered for midstream and ventricular opacification.

Figure 17:
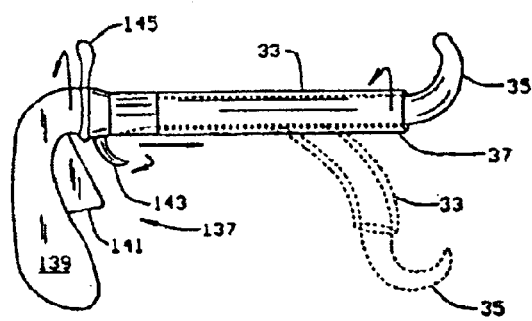
FIG. 17 is a side elevation illustrating an alternative handle design for the combination catheter of the present invention.

Turning to FIG. 17, there is shown an alternative handle mechanism 137 which is particularly suited for use with the catheter of the present invention when one-handed operations is desired. This would occur for example when the catheter of the present invention is used as an endotracheal tube and the physician's other hand is used to manipulate a laryngoscope (not shown). Handle 137 includes a pistol-grip 139 adapted to be held in the hand of a user. A first trigger 141 mounted to pistol grip 139 is suitably connected to pullwire 37 to cause sheath 33 to curve (as desired by the user) to a curved position such as that shown in phantom in FIG. 17. A second trigger 143 mounted to the pistol grip is suitably connected to the inner catheter 35 to push the inner catheter distally with respect to the sheath when actuated by the user. Handle 137 also includes a thumb actuable lever 145 to allow the user to rotate sheath 33 with respect to the handle and the inner catheter. When lever 145 is moved by the user in the direction indicated by the arrow in FIG. 17, the sheath is rotated with respect to the inner catheter 35. Note that this provides the relative motion between the sheath and the inner surgical element described in the above embodiments in a different way, in that the element which is actively rotated in this embodiment is the sheath, rather than the inner surgical element.

Figure 18:
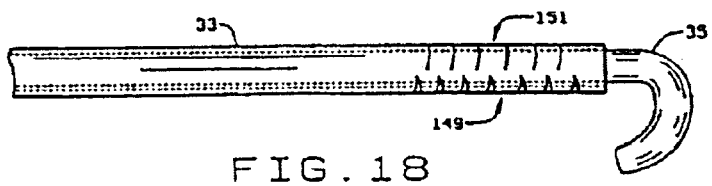
FIG. 18 is a side elevation of an alternative construction to facilitate bending of the sheath of the present invention.
Figure 19:
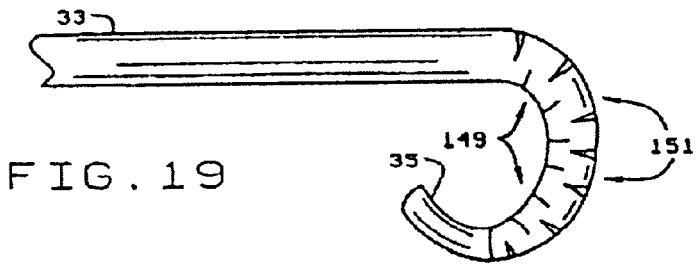
FIG. 19 is a view similar to FIG. 18 showing the sheath in a curved or bent position.

Turning to FIGS. 18 and 19, an alternative construction of sheath 33 is illustrated which includes a plurality of gaps 149 along one side of the sheath's distal end (the side which appears concave when the sheath is bent into a curved configurations) and a plurality of slits along the opposite side of the sheath's distal end. The gaps allow the sheath to readily bend in the desired direction and in a compliant manner. As the distal end of the sheath is bent (see FIG. 19), the gaps 149 close. At the same time, the slits on the opposite side of the sheath open, thereby providing greater flexibility to the distal end of the sheath. Note that the slits are superior to gaps for this purpose since they do not allow retrocurvature of the distal end of the sheath. The sheath may assume the straight position shown in FIG. 18 without resistance by the slits, but once the slits are closed further curving in that direction is opposed. It is preferred that the slits 151 be staggered with respect to the gaps 149 to provide structural integrity for the distal end of the sheath.

Figure 20:
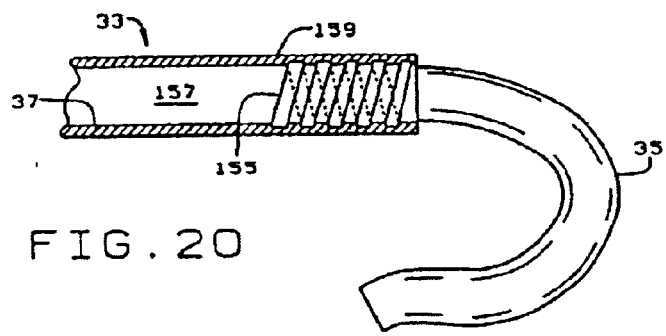
FIG. 20 is a side elevation, with parts removed for clarity, of another construction of the sheath of the present invention.

Although the curvature of the sheath is promoted by the presence of the various gaps described above in connection with the various embodiments, other structure may be used for the same purpose. For example, in FIG. 20, the distal end of sheath 33 includes a helical coil spring 155 sealed between an inner layer 157 and an outer layer 159 of thin, flexible polyurethane (or other suitable material). As the sheath 33 is curved, the coils of spring 155 close up on the concave side of the sheath, and open on the opposite side. The spring, therefore, functions in a way similar to that of the slits and gaps described above, with the additional advantage that the spring provides substantial strength to the distal end of the sheath.

Figure 21A:
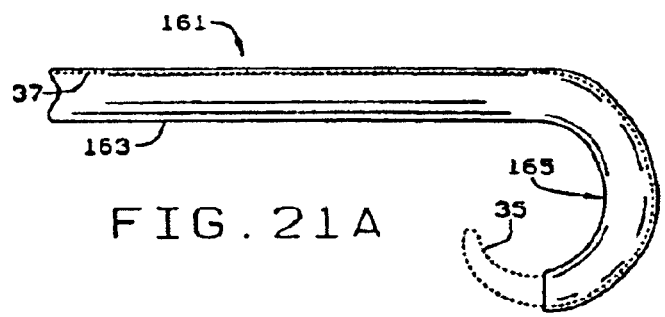
FIGS. 21A–21C illustrate an alternative construction of the sheath of the present invention in which the pullwire is used to deflect the sheath distal. tip from a curved position to a straight position.
Figure 21B:
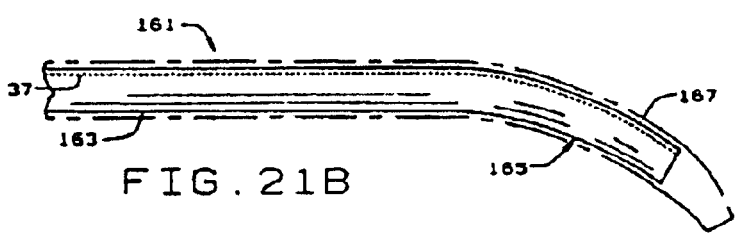
Figure 21C:

Turning to FIGS. 21A–21C, a curvable surgical element 161 is shown which operates on a somewhat different principle than those shown and described above. Surgical element 161 includes a tube 163 having a curvable or deflectable distal tip 165. Distal tip 165 is preformed in a curved shape such as that shown in FIG. 21A. Application of tension to pullwire 37 results in straightening of the distal tip to any intermediate curved shape (such as shown in FIG. 21B) and even to the straight shape shown in FIG. 21C. It should be appreciated that surgical element 161 may be used as a sheath in conjunction with an inner catheter (or other surgical element) 35 as indicated by the phantom lines in FIG. 21A. Such a sheath/inner element combination operates in the same way as described above except that the rest position for the sheath in this embodiment is curved rather than straight.

Alternatively, surgical element 161 may be used as a manipulator disposed inside another surgical element such as the catheter 167 shown in phantom in FIG. 21B.

Figure 22A:
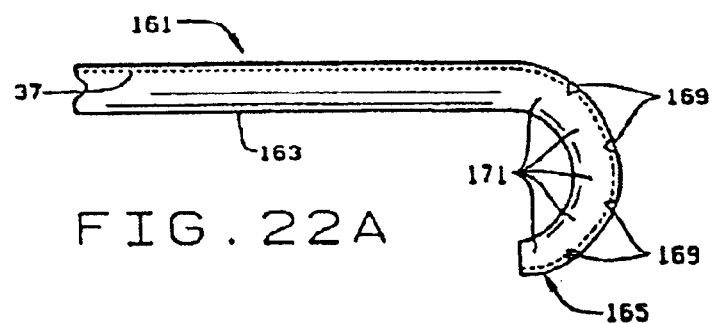
FIGS. 22A–22C are views similar to FIGS. 21A-21C showing a gap/slit construction for the sheath.
Figure 22B:
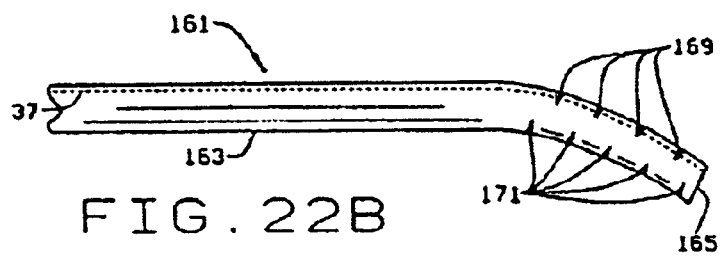
Figure 22C:
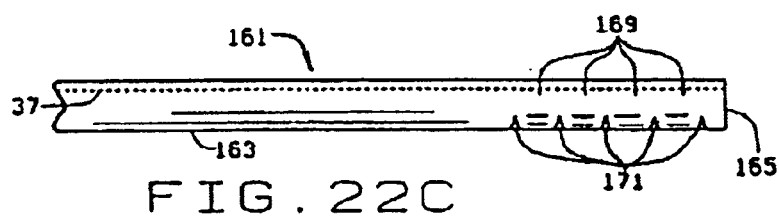

Although surgical element 161 is shown as a continuous tube in FIG. 21, it may be varied as desired to accommodate and facilitate the curving or bending of the distal tip. A plurality of gaps 169 on the convex side of distal tip 165 and a plurality of slits 171 on the concave, opposite side as shown in FIGS. 22A–22C promote accurate control of the bending of distal tip 165. As surgical element 161 is straightened, gaps 169 slowly close while slits 171 open (see FIG. 22B) until, at the straight position, gaps 169 are fully closed and slits 171 fully opened.

Other constructions could serve the same purpose. In FIGS. 23A and B, for example, a segmental band device 173 is suitably affixed to the distal end 165 of tube 163. The band device may be made of metal or plastic, and is hinged so that as the tube is straightened by application of tension to pullwire 37 the bands close together to the position shown in FIG. 23B. When the segmental band device is made of plastic, the hinging action can be accomplished with living hinges connecting the bands. Whether metal or plastic, it is preferred that the distal end of the segmental band device be suitably secured to the distal end of the tube 163.

In FIGS. 24A and 24B, an alternative embodiment of surgical element 161 is shown to include a coil spring 175 suitably wound around the distal end 165 of tube 163. Coil spring is preferably captured between two layers of polyurethane or some other suitable material as discussed above. As can be seen by comparing FIG. 24A with FIG. 24B, as the tube 163 is straightened, the spacing between the coils on the convex and concave sides of distal end 165 changes.

All these embodiments may be used as described above in connection with an inner surgical element to vary the shape and configuration of the inner surgical element as desired by the user. Furthermore, they may be used as a manipulator disposed inside a surgical element to manipulate the shape and configuration of the externally mounted surgical element similar to those described below.

A manipulator 179 of the present invention is shown in FIGS. 25–27 in combination with an externally mounted surgical element such as the catheter 181 shown in those figures. Manipulator 179 is preferably straight when in the relaxed position, as shown in FIG. 25A, although, as discussed above, a manipulator having, a relaxed curved configuration may also be used. Outer catheter 181 is disposed around manipulator 179 so that it may be moved longitudinally or rotationally with respect to the manipulator, in a manner similar to that disclosed above in connection with the other embodiments of the invention. The manipulator itself includes a pullwire 37 which may be used in the manner disclosed above to deflect the distal end of the manipulator from the straight position shown in FIG. 25A to the curved positions of FIGS. 25B and 25C. Note that outer catheter 181 is relatively flexible when compared to manipulator 181 so that bending of the distal end of the manipulator results in corresponding bending of the outer catheter. Similarly, the relatively more rigid manipulator, when rotated from the position shown in FIG. 25B to that of FIG. 25C, causes the outer catheter 181 to be rotated as well. The shape of FIG. 25C may also be achieved by rotating the manipulator while it is disposed in the straight position of FIG. 25A (in which case it does not rotate the outer catheter therewith) to the desired rotational position, and then deflecting the distal end of the manipulator (using pullwire 37). The deflection of the distal end of the manipulator bends the outer catheter into the same shape. Although the two different methods of achieving the shape of FIG. 25C would seem to be equivalent, they are not. For example, the particular vessel in which the manipulator/catheter combination is disposed may allow one method of forming the shape to be performed safely, but not the other. In addition, as discussed below in connection with FIG. 27, when the outer catheter has a curved distal end, the shapes achieved using the two methods are very different.

Turning to FIGS. 26A–26C, manipulator 179 is shown in use with a straight outer catheter 181, with the distal end of catheter 181 extended beyond the distal end of the manipulator. The use of the catheter in combination with the manipulator is thus seen to generate a number of shapes in addition to those achievable by the manipulator alone, but those shapes are limited in number. Basically, the manipulator when used with a straight outer catheter determines the entire shape of the combination device except for the length of the straight portion of the outer catheter extending distally from the distal end of the manipulator.

A vastly larger number of shapes are achievable when manipulator 179 is used with an outer catheter 183 having a curved distal end (see FIGS. 27A–27C). In fact, this combination provides the same multitude of shapes achievable with the combination catheter described above which included an outer, curvable sheath in combination with an inner catheter having a curved distal end. As can be seen by comparing FIGS. 27A and 27B, bending of the distal end of manipulator 179 results in a distal curve at the end of the manipulator/catheter combination device which exceeds the amount of curvation achievable by either the outer catheter or the manipulator alone. In addition, rotation of the manipulator with respect to the outer catheter before the distal end of the manipulator is deflected results in completely different shapes. For example, if the user were to rotate the manipulator/catheter combination of FIG. 27B, the shape of FIG. 27C would not result. That latter shape may be achieved only by rotating the manipulator with respect to the outer catheter (which is most easily accomplished when the manipulator is in the straight position shown in FIG. 27A), and then bending the manipulator to the desired position. Thus, when manipulator 179 is used with a curved outer catheter whole new families of shapes are achievable.

In fact, when the manipulator is rotated ninety degrees with respect to the curvature of the distal end of outer catheter 183 (or in general is rotated to any intermediate position between zero degrees and 180 degrees with respect to the curve of the outer catheter), out of plane curves such as that shown in FIG. 27D are achievable as well. Thus, it can be seen that the embodiment of the present invention shown in FIG. 27 is as versatile as the combination catheter embodiment of the present invention described above which used an outer, deflectable sheath. The same shapes may be achieved with both.

In view of the above, it will be seen that the various objects and features of the present invention are achieved and other advantageous results obtained. The examples of the present invention disclosed herein are intended to be illustrative, and are not to be construed in a limiting sense.

What is claimed is:

1. A method of shaping a combination catheter having an inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said lumen and being axially movable with respect to the catheter tube, at least one of said catheter tube and said inner medical element being remotely controllable to form a curve in the distal end thereof, said method comprising the steps of:

moving the combination of the catheter tube and the inner medical element in a passage in the human body to a desired position, said moving step occurring with the distal end of the inner element disposed distally of the distal tip of the catheter tube;

imaging the catheter tube and the inner medical element while said tube and medical element are disposed in the human body;

shaping the distal end of the combination catheter, during imaging of the catheter tube and the inner medical element, by manipulating the distal end of the combination catheter by remotely controlling the distal end of at least one of the catheter tube and the inner medical element to form a curve therein such that the distal end of the combination catheter takes a desired shape;

verifying the desired shape by imaging the catheter tube and the inner medical element.

2. The method as set forth in claim 1 wherein the imaging is done by fluoroscopy.

3. The method as set forth in claim 1 wherein the inner medical element is remotely controllable to assume curved configurations, said shaping step including manipulating the distal end of the inner medical element by remote control to form a curved configuration.

4. The method as set forth in claim 1 wherein one of the inner medical element and the catheter tube has a preformed curve in the distal end thereof.

5. A method of shaping a combination catheter having an inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said lumen and being axially movable in use with respect to the catheter tube, said catheter tube having a curve preformed in the distal end of the catheter tube, said inner medical element being remotely controllable to assume curved configurations, said method comprising the steps of:

moving the combination of the catheter tube and the inner medical element in a passage in the human body to a desired position;

imaging the catheter tube and the inner medical element while said tube and medical element are disposed in the human body;

shaping the distal end of the combination catheter, during imaging of the catheter tube and the inner medical element, by manipulating the distal end of the combination catheter such that the distal end of the combination catheter takes a desired shape, said shaping step including manipulating the distal end of the inner medical element by remote control to form a curved configuration;

verifying the desired shape by imaging the catheter tube and the inner medical element.

6. The method as set forth in claim 5 wherein the imaging is done by fluoroscopy.

7. A method of shaping a combination catheter having an inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said lumen and being axially movable with respect to the catheter tube, said catheter tube having a preformed curve in the distal end of the catheter tube having a first radius of curvature, said method comprising the steps of:

moving the combination of the catheter tube and the inner medical element in a passage in the human body to a desired position;

imaging the catheter tube and the inner medical element while said tube and medical element are disposed in the human body;

shaping the distal end of the combination catheter, during imaging of the catheter tube and the inner medical element, by manipulating the distal end of the combination catheter such that the distal end of the combination catheter takes a desired shape in which the distal end of the inner medical element has a second radius of curvature, said desired shape being one of a plurality of possible shapes the distal end of the combination catheter can take, the distal ends of both the catheter tube and the inner medical element being defined as extending proximally, measured from the extreme distal tip of each, only a distance not substantially greater than three times the smaller of the first and second radii of curvature;

verifying the desired shape by imaging the catheter tube and the inner medical element.

8. The method as set forth in claim 7 wherein the imaging is done by fluoroscopy.

9. The method as set forth in claim 7 wherein the inner medical element is remotely controllable to assume curved configurations, said shaping step including manipulating the distal end of the inner medical element by remote control to form a curved configuration.

10. The method as set forth in claim 7 wherein the inner medical element has a preformed curve in the distal end thereof.

11. A method of shaping a combination catheter having an inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said lumen and being axially movable with respect to the catheter tube, said catheter tube having a preformed curve in the distal end of the catheter tube having a first arc length, said method comprising the steps of:

moving the combination of the catheter tube and the inner medical element in a passage in the human body to a desired position, imaging the catheter tube and the inner medical element while said tube and medical element are disposed in the human body;

shaping the distal end of the combination catheter, during imaging of the catheter tube and the inner medical element, by manipulating the distal end of the combination catheter such that the distal end of the combination catheter takes a desired shape in which the inner medical element has a second arc length, said desired shape being one of a plurality of possible shapes the distal end of the combination catheter can take, the distal ends of both the catheter tube and the inner medical element being defined as extending proximally, measured from the extreme distal tip of each, only a distance not substantially greater than three times the smaller of the first and second arc lengths;

verifying the desired shape by imaging the catheter tube and the inner medical element.

12. The method as set forth in claim 11 wherein the imaging is done by fluoroscopy.

13. The method as set forth in claim 11 wherein the inner medical element is remotely controllable to assume curved configurations, said shaping step including manipulating the distal end of the inner medical element by remote control to form a curved configuration.

14. The method as set forth in claim 11 wherein the inner medical element has a preformed curve in the distal end thereof.

15. A method of shaping a combination catheter having an inner medical element and an outer catheter tube in which the inner medical element is disposed, said outer catheter tube having a first curve preformed in the distal end thereof, said first curve having a first radius of curvature, said catheter tube being sufficiently small so that the catheter tube may be inserted into the human body and having a lumen in which the inner medical element is disposed, said inner medical element being disposed in said lumen, having, a second curve preformed in the distal end thereof, and being axially movable with respect to the catheter tube, said second curve having a second radius of curvature, said method comprising the steps of:

moving the combination of the catheter tube and the inner medical element in a passage in the human body to a desired position;

imaging the catheter tube and the inner medical element while said tube and medical element are disposed in the human body;

shaping the distal end of the combination catheter, during imaging, by manipulating the distal end of the combination catheter such that the distal end of the combination catheter takes a desired shape, said desired shape being one of a plurality of possible shapes the distal end of the combination catheter can take;

the distal ends of both the catheter tube and the inner medical element being defined as extending proximally, measured from the extreme distal tip of each, only a distance not substantially greater than three times the smaller of the first and second radii of curvature;

verifying the desired shape by imaging.

16. A method of shaping a combination catheter having a polymeric inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said lumen and being axially movable with respect to the catheter tube, at least one of said catheter tube and said polymeric inner medical element being remotely controllable to form a curve in the distal end thereof, said method comprising the steps of:

moving the combination of the catheter tube and the polymeric inner medical element in a passage in the human body to a desired position;

imaging the catheter tube and the polymeric inner medical element while said tube and medical element are disposed in the human body;

shaping the distal end of the combination catheter, during imaging of the catheter tube and the inner medical element, by manipulating the distal end of the combination catheter such that the distal end of the combination catheter takes a desired shape, said desired shape being one of a plurality of possible shapes the distal end of the combination catheter can take, said shaping including manipulating the distal end of at least one of the inner medical element and the catheter tube by remote control to form a curved configuration;

verifying the desired shape by imaging the catheter tube and the inner medical element.

17. The method as set forth in claim 16 wherein the imaging is done by fluoroscopy.

18. The method as set forth in claim 16 wherein the inner medical element is remotely controllable to assume curved configurations, said shaping step including remotely controlling the inner medical element to assume a curved configuration.

19. The method as set forth in claim 16 wherein one of the inner medical element and the catheter tube has a preformed curve in the distal end thereof.

20. A method of manipulating the shape of a combination catheter in a human body comprising:

inserting a catheter tube into a human body, said catheter tube having a wall and an internal lumen extending substantially through the length of the catheter tube, said catheter tube having an outside diameter sufficiently small so that the catheter tube may be inserted into the human body, said catheter tube having a proximal end and a distal end, said catheter tube further having remote control apparatus extending from the proximal end of the catheter tube for deflecting the distal end of the catheter tube;

disposing an inner medical element disposed in the lumen of the catheter tube, said inner medical element having a distal end performed in a curved configuration independent of the catheter tube, said catheter tube and said inner medical element constituting a combination catheter;

imaging the combination catheter while it is in the human body;

modifying the shape of the distal end of the combination catheter during imaging by relative manipulation of the inner medical element and the outer catheter tube, said shaping step including manipulating the distal end of the catheter tube by remote control to form a curved configuration.

21. The method as set forth in claim 20 wherein the inner medical element and the outer catheter tube are fixed in place with respect to each other once the shape of the distal end of the combination catheter is modified.

22. The method as set forth in claim 20 wherein the imaging is done fluoroscopically.

23. A method of manipulating the shape of a combination catheter in a human body comprising:

inserting a catheter tube into a human body, said catheter tube having a wall and an internal lumen extending substantially through the length of the catheter tube, said catheter tube having an outside diameter sufficiently small so that the catheter tube may be inserted into the human body, said catheter tube having a proximal end and a distal end, said catheter tube further having a preformed curve in the distal end of the catheter tube;

disposing an inner medical element disposed in the lumen of the catheter tube, said inner medical element having remote control apparatus for selectively forming curved configurations of the inner medical element independent of the catheter tube, said catheter tube and said inner medical element constituting a combination catheter;

imaging the combination catheter while it is in the human body;

modifying the shape of the distal end of the combination catheter during imaging by relative manipulation of the inner medical element and the outer catheter tube, said modifying of the shape including axial movement of the inner medical element with respect to the catheter tube during operation and manipulating the distal end of the inner medical element by remote control to form a curved configuration.

24. The method as set forth in claim 23 wherein the inner medical element and the outer catheter tube are fixed in place with respect to each other once the shape of the distal end of the combination catheter is modified.

25. The method as set forth in claim 23 wherein the imaging is done fluoroscopically.

26. A method of manipulating the shape of a combination catheter in a human body comprising:

inserting a catheter tube into a human body, said catheter tube having a wall and an internal lumen extending substantially through the length of the catheter tube, said catheter tube having an outside diameter sufficiently small so that the catheter tube may be inserted into the human body, said catheter tube having a proximal end and a distal end, said catheter tube further having a preformed curve in the distal end of the catheter tube, said preformed curve having a first arc length;

disposing an inner medical element disposed in the lumen of the catheter tube, said inner medical element having a distal end with a preformed curve, said preformed curve having a second arc length, said catheter tube and said inner medical element constituting a combination catheter;

the distal end of the catheter tube being defined as extending proximally from the extreme distal tip of the catheter tube only a distance not substantially greater than three times the smaller of the first and second arc lengths, the distal end of the inner medical element being defined as extending proximally from the extreme distal tip of the inner medical element only a distance not substantially greater than three times the smaller of the first and second arc lengths;

imaging the combination catheter while it is in the human body;

modifying the shape of the distal end of the combination catheter during imaging by relative manipulation of the inner medical element and the outer catheter tube to form a desired shape, said desired shape being one of a plurality of possible shapes the distal end of the combination catheter can take.

27. The method as set forth in claim 26 wherein the inner medical element and the outer catheter tube are fixed in place with respect to each other once the shape of the distal end of the combination catheter is modified.

28. The method as set forth in claim 26 wherein the imaging is done fluoroscopically.

29. A method of manipulating the shape of a combination catheter in a human body comprising:

inserting a catheter tube into a human body, said catheter tube having a wall and an internal lumen extending substantially through the length of the catheter tube, said catheter tube having an outside diameter sufficiently small so that the catheter tube may be inserted into the human body, said catheter tube having a proximal end and a distal end, said catheter tube further having a preformed curve in the distal end of the catheter tube, said preformed curve having a first radius of curvature;

disposing an inner medical element disposed in the lumen of the catheter tube, said inner medical element having a distal end with a preformed curve, said preformed curve having a second radius of curvature, said catheter tube and said inner medical element constituting a combination catheter;

the distal end of the catheter tube being defined as extending proximally from the extreme distal tip of the catheter tube only a distance not substantially greater than three times the smaller of the first and second radii of curvature, the distal end of the inner medical element being defined as extending proximally from the extreme distal tip of the inner medical element only a distance not substantially greater than three times the smaller of the first and second radii of curvature;

imaging the combination catheter while it is in the human body;

modifying the shape of the distal end of the combination catheter during imaging by relative manipulation of the inner medical element and the outer catheter tube to form a desired shape, said desired shape being one of a plurality of possible shapes the distal end of the combination catheter can take.

30. The method as set forth in claim 29 wherein the inner medical element and the outer catheter tube are fixed in place with respect to each other once the shape of the distal end of the combination catheter is modified.

31. The method as set forth in claim 29 wherein the imaging is done fluoroscopically.

32. A method of shaping a combination catheter having an inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said lumen and being axially movable with respect to the catheter tube during operation, at least one of said catheter tube and said inner medical element being remotely controllable to form a curve in the distal end thereof, said method comprising the steps of:

moving the combination of the catheter tube and the inner medical element in a passage in the human body to a desired position;

imaging the catheter tube and the inner medical element while said tube and medical element are disposed in the human body;

shaping the distal end of the combination catheter, during imaging of the catheter tube and the inner medical element, by manipulating the distal end of the combination catheter such that the distal end of the combination catheter takes a desired shape, said desired shape being one of a plurality of possible shapes the distal end of the combination catheter can take, said manipulating step including moving the inner medical element axially with respect to the catheter tube;

verifying the desired shape by imaging the catheter tube and the inner medical element.

33. The method as set forth in claim 32 wherein the imaging is done by fluoroscopy.

34. The method as set forth in claim 32 wherein the inner medical element is remotely controllable to assume curved configurations.

35. The method as set forth in claim 32 wherein one of the inner medical element and the catheter tube has a preformed curve in the distal end thereof.

36. A method of shaping a combination catheter having an inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said catheter tube lumen, said inner medical element having a lumen extending therethrough for passage of fluid between the proximal end and the distal end of the combination catheters said inner medical element further being axially movable with respect to the catheter tube, at least one of said catheter tube and said inner medical element being remotely controllable to form a curve in the distal end thereof, said method comprising the steps of:

moving the combination of the catheter tube and the inner medical element in a passage in the human body to a desired position;

imaging the catheter tube and the inner medical element while said tube and medical element are disposed in the human body;

shaping the distal end of the combination catheter, during imaging of the catheter tube and the inner medical element, by manipulating the distal end of the combination catheter such that the distal end of the combination catheter takes a desired shape, said desired shape being one of a plurality of possible shapes the distal end of the combination catheter can take;

verifying the desired shape by imaging the catheter tube and the inner medical element;

passing fluid through the lumen of the inner medical element.

37. The method as set forth in claim 36 wherein the imaging is done by fluoroscopy.

38. The method as set forth in claim 36 wherein the inner medical element is remotely controllable to assume curved configurations.

39. The method as set forth in claim 36 wherein one of the inner medical element and the catheter tube has a preformed curve in the distal end thereof.

40. A method of shaping a combination catheter having an inner medical element and an outer catheter tube in which the inner medical element is disposed, said outer catheter tube being sufficiently small so that the catheter tube may be inserted into the human body, said catheter tube having a lumen in which the inner medical element is disposed, said inner medical element being disposed in said lumen and being axially movable with respect to the catheter tube, said catheter tube being remotely controllable to form a curve in the distal end of the catheter tube, said method comprising the steps of:

moving the combination of the catheter tube and the inner medical element in a passage in the human body to a desired position;

imaging the catheter tube and the inner medical element while said tube and medical element are disposed in the human body;

shaping the distal end of the combination catheter, during imaging of the catheter tube and the inner medical element, by manipulating the distal end of the combination catheter such that the distal end of the combination catheter takes a desired shape, said desired shape being one of a plurality of possible shapes the distal end of the combination catheter can take, said shaping including manipulating the distal end of the catheter tube by remote control to form a curved configuration;

verifying the desired shape by imaging the catheter tube and the inner medical element.

41. The method as set forth in claim 40 wherein the imaging is done by fluoroscopy.

42. The method as set forth in claim 40 wherein the inner medical element is remotely controllable to assume curved configurations.

43. The method as set forth in claim 40 wherein the inner medical element has a preformed curve in the distal end thereof.

44. A method of shaping a combination catheter having an inner medical element and an outer catheter tube in which the inner medical element is disposed, said outer catheter tube having a first curve preformed in the distal end thereof, said first curve having a first arc length, said catheter tube being sufficiently small so that the catheter tube may be inserted into the human body and having a lumen in which the inner medical element is disposed, said inner medical element being disposed in said lumen, having a second curve preformed in the distal end thereof, and being axially movable with respect to the catheter tube, said second curve having a second arc length, said method comprising the steps of;

moving the combination of the catheter tube and the inner medical element in a passage in the human body to a desired position;

imaging the catheter tube and the inner medical element while said tube and medical element are disposed in the human body;

shaping the distal end of the combination catheter, during imaging, by manipulating the distal end of the combination catheter such that the distal end of the combination catheter takes a desired shape, said desired shape being one of a plurality of possible shapes the distal end of the combination catheter can take;

the distal ends of both the catheter tube and the inner medical element being defined as extending proximally, measured from the extreme distal tip of each, only a distance not substantially greater than three times the smaller of the first and second arc lengths;

verifying the desired shape by imaging.

* * * * *